(12) United States Patent
Udipi et al.

(10) Patent No.: US 8,518,097 B2
(45) Date of Patent: Aug. 27, 2013

(54) PLASTICIZED STENT COATINGS

(75) Inventors: Kishore Udipi, Santa Rosa, CA (US); Peiwen Cheng, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 3043 days.

(21) Appl. No.: 10/831,091

(22) Filed: Apr. 23, 2004

(65) Prior Publication Data

US 2004/0215336 A1    Oct. 28, 2004

Related U.S. Application Data

(60) Provisional application No. 60/465,526, filed on Apr. 25, 2003.

(51) Int. Cl.
*A61F 2/84* (2006.01)
(52) U.S. Cl.
USPC ........................................ 623/1.11; 623/1.42

(58) Field of Classification Search
USPC .................... 623/1.42, 1.43, 1.15, 1.44–1.46, 623/1.11; 424/423
See application file for complete search history.

(56) References Cited

U.S. PATENT DOCUMENTS

| 4,929,510 | A | 5/1990 | Ruckenstein et al. |
| 5,756,553 | A * | 5/1998 | Iguchi et al. ............... 514/772.3 |
| 6,214,901 | B1 | 4/2001 | Chudzik et al. |
| 6,270,788 | B1 | 8/2001 | Koulik et al. |
| 6,335,029 | B1 | 1/2002 | Kamath et al. |
| 2001/0007081 | A1* | 7/2001 | Caprio et al. ................ 623/1.11 |
| 2002/0099438 | A1* | 7/2002 | Furst ........................... 623/1.16 |

FOREIGN PATENT DOCUMENTS

| EP | 1273314 | 1/2003 |
| WO | 0224247 | 3/2002 |
| WO | 03082368 | 10/2003 |
| WO | 03099346 | 12/2003 |

* cited by examiner

*Primary Examiner* — Ryan Severson

(57) ABSTRACT

The present invention provides a system for treating a vascular condition, including a catheter, a stent with a stent framework operably coupled to the catheter, and a drug-polymer coating on the stent framework including at least one plasticizer dispersed within the drug-polymer coating.

31 Claims, 5 Drawing Sheets

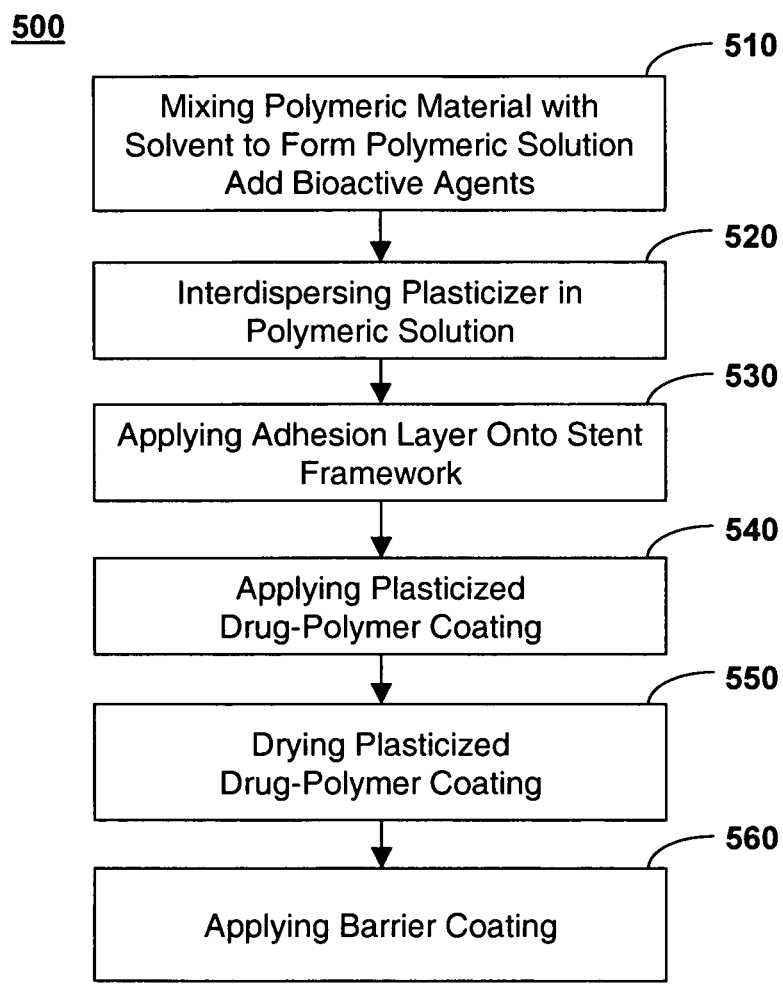

PLASTICIZED STENT COATINGS

RELATED APPLICATION

This application claims priority to U.S. Provisional Application No. 60/465,526, "Plasticized Stent Coatings" to Kishore Udipi and Peiwen Cheng, filed Apr. 25, 2003, the entirety of which is incorporated by reference.

FIELD OF THE INVENTION

This invention relates generally to biomedical stents. More specifically, the invention relates to a drug-polymer coating with a dispersed bioactive drug and at least one plasticizer on an endovascular stent for in vivo, timed-release drug delivery.

BACKGROUND OF THE INVENTION

Drug-coated stents can improve the overall effectiveness of angioplasty and stenotic procedures performed on the cardiovascular system and other vessels within the body by delivering potent therapeutic compounds at the point of infarction. Drugs such as anti-inflammatants and anti-thrombogenics may be dispersed within the drug-polymer coating and released in a controlled manner after the insertion and deployment of a stent. These drugs and coatings can reduce the trauma to the local tissue bed, aid in the healing process, and significantly reduce the narrowing or constriction of the blood vessel that can reoccur where the stent is placed.

Stenting procedures have had a major impact on the field of interventional cardiology and endovascular surgery. Much medical research and development in the last decade have been dedicated to stents, and in the most recent years, to drug-eluting coatings for stents. The efficacy of vascular stents is potentially increased by the addition of stent coatings that contain pharmaceutical drugs. These drugs may be released from the coating while in the body, delivering their patent effects at the site where they are most needed. Thus, the localized levels of the medications can be elevated, and therefore potentially more effective than orally- or intravenously-delivered drugs that distribute throughout the body, the latter which may have little effect on the impacted area, or which may be expelled rapidly from the body without achieving their pharmaceutical intent. Furthermore, drugs released from tailored stent coatings may have controlled, timed-release qualities, eluting their bioactive agents over hours, weeks or even months.

In practice, a common solvent or pair of solvents is used to dissolve the drug and polymer. The polymer may include copolymers or polymer blends. Then the drug-polymer solution is sprayed on the stents. Upon drying, the drug-polymer is formed on the stent surface. In this process, the drug-polymer ratio and polymer content for each formulation are fixed.

When the drug-coated stent is deployed in a vessel in the body, the drug release is predominantly based on a diffusion mechanism. Drug diffusion is controlled in part by the molecular size, the crystallinity, and the hydrophilic-lipophilic balance of the drug, as well as the morphology of the polymeric coating, the glass temperature Tg of the polymer and the polymer crystallinity. For most drugs, there is a common releasing profile: a burst release occurs where a large amount of drug gets released initially, followed by a slow, gradual release that leads to a gradually decaying effect where drug elution from the stent diminishes with time. This typical releasing profile occurs because of the resistance offered by the polymer film to the transport of drug to the surface, and the reduction of the drug supply from within the coating.

Several classes of drug-polymer chemistries have been explored for use in stent coatings, as found in the current art. A composition with a bioactive agent for coating the surface of a medical device based on poly (alkyl)(meth)acrylate and poly(ethyline-co-vinyl acetate) is described in "Bioactive Agent Release Coating," Chudzik et al., U.S. Pat. No. 6,214,901, issued Apr. 10, 2001. A composite polymer coating with a bioactive agent and a barrier coating formed in situ by a low-energy plasma polymerization of a monomer gas is described in U.S. Pat. No. 6,335,029, "Polymeric Coatings for Controlled Delivery of Active Agents," K. R. Kamath et al., issued Jan. 1, 2002. Another polymeric coating for an implantable medical article is presented in "Implantable Medical Device," E. Koulik et al., U.S. Pat. No. 6,270,788, issued Aug. 7, 2001. This stent coating is based on hydrophobic methacrylate and acrylate monomers, a functional monomer having pendant chemically reactive amino groups capable of forming covalent bonds with biologically active compounds, and a hydrophilic monomer, wherein a biomolecule is coupled to the coated surface. Use of block copolymers on a hydrophobic polymer substrate is described in "Biocompatible Polymer Articles," E. Ruckenstein et al., U.S. Pat. No. 4,929,510, issued May 29, 1990.

In selecting polymers for drug delivery, three important criteria must be met: polymer biocompatibility, satisfactory mechanical properties such as durability and integrity during roll down and expansion of the stent, and correct release profiles for the drugs. Candidate chemistries for drug polymers may result in an excessively rapid elution of an incorporated drug. When a drug is eluted too quickly, it may be ineffective. When a drug is eluted too slowly, the pharmaceutical intent may remain unfulfilled. Furthermore, if insufficient drug is delivered after stent deployment, the potential benefits of time-released drugs may be compromised by inadequate dosages.

Unfortunately, some drug polymers do not provide the mechanical flexibility necessary to be effectively used on a stent. A stent may be deployed by self-expansion or balloon expansion, accompanied by a high level of bending at portions of the stent framework, which can cause cracking, flaking, peeling, or delaminating of many candidate drug polymers while the stent diameter is increased by threefold or more during expansion. The candidate drug polymer may not stick or adhere. Furthermore, the coating may fall off, crystallize or melt during preparation and sterilization prior to deployment, further limiting the types of drug polymers acceptable for use on cardiovascular stents.

It is desirable to have a medicated stent that can be tailored to provide a desired elution rate profile for one or more drugs, without compromising the mechanics of the stent during deployment and use. A preferred drug-polymer system can be tailored to accommodate a variety of drugs for controlled time delivery, while maintaining mechanical integrity during stent deployment. Of additional benefit is a polymeric system that can be readily altered to control the elution rate of interdispersed bioactive drugs and to control their bioavailability Furthermore, a more desirable polymer-drug system can be tailored to enhance or diminish the burst effect of drug delivery after stent deployment, and to enhance the ability to deliver drugs over extended periods of time.

It is an object of this invention, therefore, to provide a framework and structure for effective, controlled delivery of suitable quantities of pharmaceutical agents from medicated stents. Additional objects of this invention include providing a system and method for treating heart disease and other vascular conditions, providing methods of manufacturing drug-polymer coated stents, and overcoming the deficiencies and limitations described above.

SUMMARY OF THE INVENTION

One aspect of the invention provides a system for treating a vascular condition, including a catheter, a stent including a stent framework operably coupled to the catheter, and a drug-polymer coating including at least one plasticizer operably disposed on the stent framework.

Another aspect of the invention is a drug-polymer stent comprising a stent framework and a plasticized drug-polymer coating on the stent framework.

Another aspect of the invention is a method of manufacturing a drug-polymer coated stent, including the steps of mixing a polymeric material with a solvent to form a polymeric solution; interdispersing a plasticizer in the polymeric solution to form a plasticized drug-polymer coating; applying the plasticized drug-polymer coating onto a stent framework, and drying the plasticized drug-polymer coating.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

FIG. 5 is a flow diagram of a method of manufacturing a drug-polymer coated stent, in accordance with one embodiment of the current invention.

DETAILED DESCRIPTION OF THE PRESENTLY PREFERRED EMBODIMENTS

Figure 1:
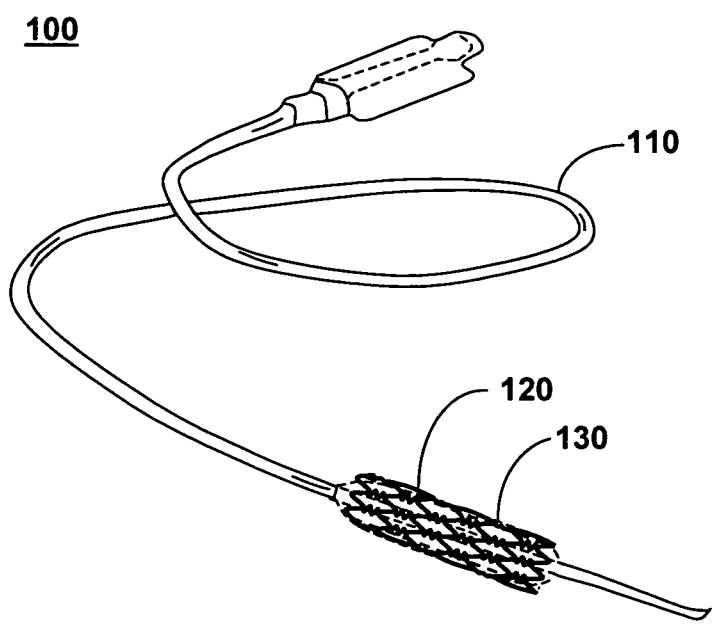
FIG. 1 is an illustration of a system for treating a vascular condition including a catheter, a stent coupled to the catheter, and a drug-polymer coating including at least one plasticizer, in accordance with one embodiment of the current invention.

FIG. 1 shows an illustration of a system for treating a vascular condition including a catheter 110, a stent including a stent framework 120 coupled to the catheter, and a drug-polymer coating 130 on stent framework 120, the drug-polymer coating including at least one plasticizer dispersed within the drug-polymer coating, in accordance with one embodiment of the present invention at 100. The plasticizers within the drug-polymer coating modulate the release of incorporated drugs from the coatings. The system may be used in the treatment of heart disease, various cardiovascular ailments, and other vascular conditions using catheter-deployed endovascular stents with plasticized drug-polymer coatings and other polymer coatings disposed on the stent frameworks for controlling the release and phasing of bioactive agents and drugs from the drug polymer. Treating vascular conditions refers to the prevention or correction of various ailments and deficiencies associated with the cardiovascular system, urinogenital systems, biliary conduits, abdominal passageways and other biological vessels within the body using stenting procedures.

Speeding the transport of drug from the inner layers of the drug-polymer coating 130 to the outer edge is accomplished through the addition of suitable plasticizers into the drug polymer. Plasticizers are small, bulky molecules that can improve the flexibility of polymeric materials, and also allow more drugs to be loaded in the drug-polymer. The plasticizers have good compatibility with the polymer but not so much as to have a solvent effect. This optimum compatibility helps to retain the plasticizer in the film and not to exude. These small, bulky molecules tend to separate the polymer chains from each other and reduce the cohesive force, thereby making the polymer coating more flexible. Separating polymer chains, in addition to flexibilizing the coatings, also facilitates the transport of the drug from the inner layers to the outer layers. Drugs located near the outer surface of the drug-polymer coating tend to be eluted first, whereas drugs nearer the stent framework are exuded later. Since drugs nearer the stent framework have an effectively thicker polymer layer to diffuse through before the drug leaves the coating, the elution rate tends to be slower. Additionally, since the diffusion process is driven in part by the concentration of the drugs in the drug polymer, the elution rate will naturally tend to be reduced as the concentration of drugs diminishes and as the amount of drug in the drug polymer lessens. Adding plasticizers, particularly to the inner layers of the drug polymer, can help in overcoming the burst effect and in maintaining a steady and more controlled release profile.

In this embodiment, catheter 110 may include a balloon used to expand the stent, or a sheath that retracts to allow expansion of the stent. Drug-polymer coating 130 includes one or more bioactive agents that provide a therapeutic characteristic. The bioactive agent is a pharmacologically active drug or bioactive compound. Drug-polymer coating 130 may include another polymer layer such as a cap coating or barrier coating, or another drug polymer. The polymer layer provides a controlled drug-elution characteristic for each bioactive agent or drug. Drug elution refers to the transfer of the bioactive agent out from drug polymer coating 130. Drug elution is determined as the total amount of bioactive agent excreted out of the drug polymer, typically measured in units of weight such as micrograms, or in weight per peripheral area of the stent. In one embodiment, the drug polymer includes between 0.5 percent and 50 percent of the bioactive agent of drug by weight.

Upon insertion of catheter 110 and stent framework 120 with drug-polymer coating 130 into a directed vascular region of a human body, stent framework 120 may be expanded by applying pressure to a balloon positioned inside the stent, or by retracting a sheath to allow expansion of a self-expanding stent. Balloon deployment of stents and self-expanding stents are well known in the art.

Stent framework 120 is typically oriented cylindrically such that an exterior surface of the stent framework contacts the vessel wall when deployed in the body, and an interior surface of the stent framework is in contact with the blood or other bodily fluids flowing through the vessel. Stent framework 120 may comprise a metallic base or a polymeric base.

The metallic base may comprise a material such as stainless steel, nitinol, tantalum, MP35N alloy, platinum, titanium, a suitable biocompatible alloy, or any combination thereof. Stent framework 120 may comprise any suitable biocompatible polymer.

Drug-polymer coating 130 includes one or more bioactive drugs or agents to provide a therapeutic characteristic. The bioactive agents provide treatment or prevention of one or more conditions including coronary restenosis, cardiovascular restenosis, angiographic restenosis, arteriosclerosis, hyperplasia, and other diseases and conditions. For example, the bioactive agent can be selected to inhibit or prevent vascular restenosis, a condition corresponding to a narrowing or constriction of the diameter of the bodily lumen where the stent is placed. In one embodiment, the bioactive drug comprises an antirestenotic agent such as rapamycin, a macrolide antibiotic that possesses immuno-suppressant activity. In another embodiment, the bioactive drug comprises a bioactive agent such as an antisense agent, antirestenotic agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative. In another embodiment, drug-polymer coating 130 includes a combination of bioactive agents. For example, a first bioactive drug may comprise an antirestenotic drug such as rapamycin or a rapamycin derivative, and a second bioactive drug may comprise an anti-inflammatory drug such as dexamethosone.

Drug-polymer coating 130 is positioned on stent framework 120. Various drugs are loaded into drug-polymer coating 130 on stent framework 120. Different types of drugs and polymers may be included in drug-polymer coating 130, for example, for release of drugs at various stages of restenosis. In one embodiment, the drug-polymer coated stent comprises a drug-polymer coating 130 where drug polymers are deposited in layers. Optionally, polymer membranes or barrier layers may be positioned in between the drug-polymer layers for controlled release of various drugs. Drugs such as anti-proliferatives, anti-inflammatants, anti-thrombotic drugs, antisense drugs, gene therapies and therapeutic peptides can be loaded on the stent for delivery during the different stages of the restenotic process. The drugs in the form of drug polymers may be deposited in layers with polymer membranes in between for controlled release. Drugs in the form of microspheres, powders, and other forms may also be positioned in the drug-polymer coating. Applications of the drug-polymer stent include restenotic treatments of coronary blood vessels after balloon angioplasty and stenting, treatment of in-stent hyperplasia, and local drug delivery to blood vessel walls.

A cap coating or barrier coating may be positioned on drug-polymer coating 130. The barrier coating also can be used for the delivery of drugs. For example, an antithrombotic drug such as hirudin or heparin can be incorporated into the outer polymer membrane for the prevention of acute thrombosis. The barrier coating may cover a portion or the entire stent framework in addition to drug-polymer coating 130. An adhesion layer may be positioned between stent framework 120 and drug-polymer coating 130 to assist in adhesion between stent framework 120 and drug-polymer coating 130.

Figure 2:
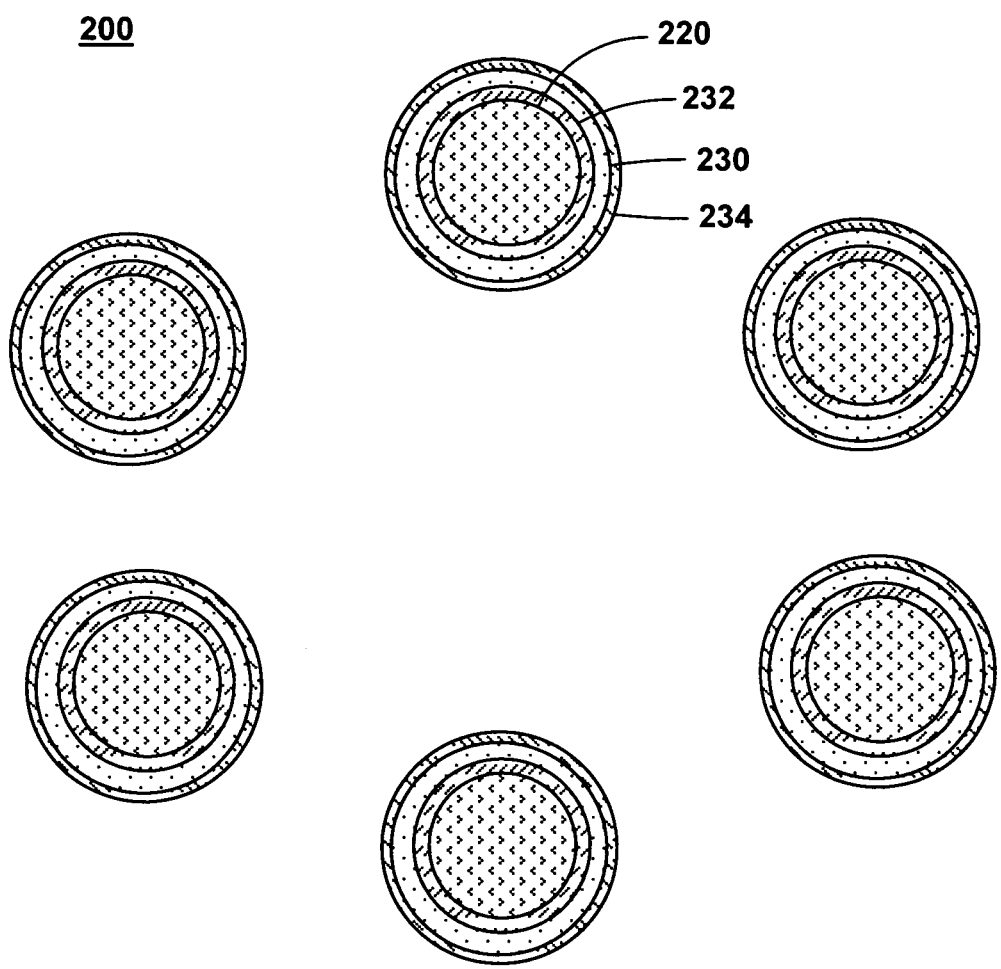
FIG. 2 is a cross-sectional view of a drug-polymer coated stent, in accordance with one embodiment of the current invention.

FIG. 2 shows a cross-sectional view of a drug-polymer coated stent in accordance with one embodiment of the current invention at 200. Drug-polymer coated stent 200 comprises a stent framework 220 and a plasticized drug-polymer coating 230 operably disposed on stent framework 220. Drug-polymer coated stent 200 may also include an adhesion layer 232, additional drug-polymer layers, and a cap or barrier coating 234.

Stent framework 220 may comprise a metallic base or a polymeric base. The base may comprise, for example, stainless steel, nitinol, tantalum, MP35N alloy, platinum, titanium, a suitable biocompatible alloy, a suitable biocompatible material, a suitable polymeric material, or a combination thereof.

Drug-polymer coating 230 is operably disposed on the stent framework. The drug-polymer coating includes at least one bioactive agent to provide a therapeutic characteristic. Drug-polymer coating 230 includes at least one plasticizer.

The bioactive agent within drug-polymer coating 230 may include, for example, antirestonotic agent, an antineoplastic agent, an antiproliferative agent, an antisense agent, an antiplatelet agent, an antithrombogenic agent, an anticoagulant, an antibiotic, an anti-inflammatory agent, a gene therapy agent, an organic drug, a pharmaceutical compound, a recombinant DNA product, a recombinant RNA product, a collagen, a collagenic derivative, a protein, a protein analog, a saccharide, a saccharide derivative, or a combination thereof. For example, an antirestenotic agent such as rapamycin or rapamycin derivatives prevents or reduces the recurrence of narrowing and blockage of the bodily vessel. An antisense drug works at the genetic level to interrupt the process by which disease-causing proteins are produced. An antineoplastic agent is typically used to prevent, kill, or block the growth and spread of cancer cells in the vicinity of the stent. An antiproliferative agent may prevent or stop targeted cells or cell types from growing. An antithrombogenic agent actively retards blood clot formation. An anticoagulant often delays or prevents blood coagulation with anticoagulant therapy, using compounds such as heparin and coumarins. An antiplatelet agent may be used to act upon blood platelets, inhibiting their function in blood coagulation. An antibiotic is frequently employed to kill or inhibit the growth of microorganisms and to combat disease and infection. An anti-inflammatory agent such as dexamethasone can be used to counteract or reduce inflammation in the vicinity of the stent. At times, a steroid is used to reduce scar tissue in proximity to an implanted stent. A gene therapy agent may be capable of changing the expression of a person's genes to treat, cure or ultimately prevent disease.

By definition, a bioactive agent is any therapeutic substance that provides prevention or treatment of disease or disorders. An organic drug is any small-molecule therapeutic material. A pharmaceutical compound is any compound that provides a therapeutic effect. A recombinant DNA product or a recombinant RNA product includes altered DNA or RNA genetic material. Bioactive agents of pharmaceutical value may also include collagen and other proteins, saccharides, and their derivatives. The molecular weight of the bioactive agent typically ranges from 200 to 60,000 Dalton and above.

Drug-polymer coating 230 includes at least one plasticizer. The plasticizer tends to separate the polymeric chains, which may add more flexibility to the drug-polymer coating, allow more drugs to be contained in the drug polymer, and aid in the control of the diffusion of the drugs from the interior of the drug-polymer to the outside surface, where it is eluded into the surrounding tissue and fluids. The plasticizer may include, for example, lecithin, dibutyl sebacate, citric acid, an alcohol ester, polyethylene glycol, polypropylene glycol, a biostable plasticizer, a biocompatible plasticizer, a biodegradable plasticizer, or a combination thereof. The plasticized drug-polymer coating typically has a thickness between 0.1 microns and 50 microns. Drug-polymer coating 230 covers at least a portion of stent framework 220.

Drug-polymer coated stent 200 may also include an adhesion layer 232, which is positioned between stent framework 220 and drug-polymer coating 230. The adhesion layer enhances the bond strength between the drug-polymer coating and the stent framework, particularly with metallic stent frameworks. Adhesion layer 232 comprises a material such as, for example, parylene, polyurethane, phenoxy, epoxy, polyimide, polysulfone, pellathane, a suitable polymeric adhesion material, or a combination thereof. The adhesion layer typically has a thickness between 0.1 microns and about 2.0 microns. Adhesion layer 232 may cover all or a portion of stent framework 220.

Drug-polymer coated stent 200 may also include barrier coating 234, sometimes referred to as a cap coating, which covers the plasticized drug-polymer coating. Barrier coating 234 is typically a polymeric membrane and aids in the control of the elution of drugs from the drug-polymer coating. Barrier coating 234 may include, for example, a polyurethane, a phenoxy, ethylene vinyl acetate, polycaprolactone, polylactide, fibrin, collagen, a biocompatible polymer, a biostable polymer, a biodegradable polymer, or a combination thereof. The barrier coating has a thickness typically between 0.1 microns and 10 microns. Barrier coating 234 may cover all or part of drug-polymer coating 230, and may cover all or part or stent framework 220.

Figure 3:
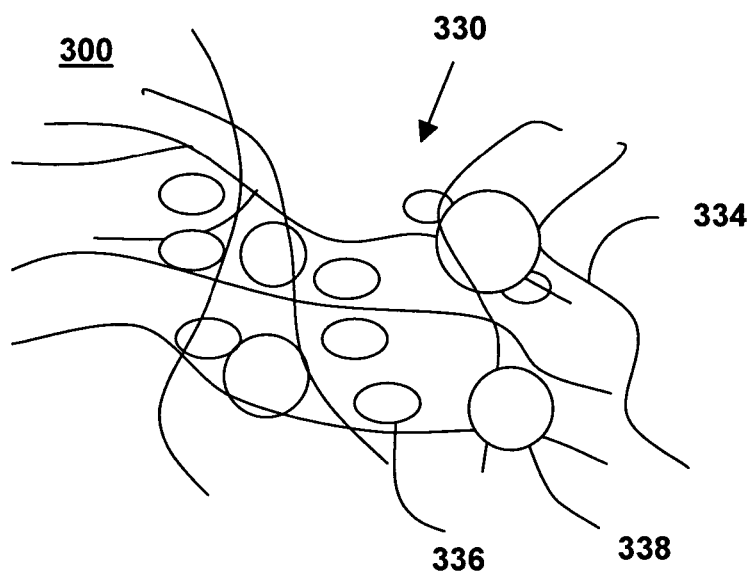
FIG. 3 is a schematic illustration of a drug-polymer coating with at least one plasticizer interdispersed within the drug-polymer coating, in accordance with one embodiment of the current invention.

FIG. 3 shows a schematic illustration of a drug-polymer coating with at least one plasticizer interdispersed within the drug-polymer coating, in accordance with one embodiment of the present invention at 300. The pictorial illustration depicts a drug-polymer coating 330, which includes polymer chains 334, drug molecules 336, and at least one plasticizer 338 dispersed within the drug-polymer coating.

Polymer chains 334 may comprise any suitable polymer chain of small, medium or large molecular weights that can be less than 200 Daltons or exceed 500,000 Daltons. Polymeric chains 334 may be amorphous, crystalline or a combination thereof. Polymeric chains 334 may comprise, for example, a linear polymer, a block copolymer, or a polymer blend. Polymeric chains 334 may be networked or cross-linked. Polymeric chains 334 may have a preferred orientation, though are usually disposed randomly.

Drug molecules 336 are interdispersed within the drug-polymer. The drugs typically have a smaller molecular weight than the polymers, and may be mixed in with the polymers. The drugs may be attached to the ends or grafted onto polymer chains 334 at various sites along their length. Drug molecules 336 may include, for example, various organic and pharmaceutical compounds that have a therapeutic characteristic.

Plasticizers 338 comprise shorter, bulkier molecules. Plasticizers 338 tend to separate polymer chains 334 from one another, providing additional flexibility to the drug polymer. Plasticizers 338 separate polymer chains 334 and can provide additional locations for drug molecules 336 to reside. Examples of plasticizers suitable for use in drug-polymer coatings include lecithin, dibutyl sebacate, citric acid, an alcohol ester, polyethylene glycol, polypropylene glycol, a biostable plasticizer, a biocompatible plasticizer, a biodegradable plasticizer, or combinations thereof.

Drug molecules 336 may be released from drug-polymer coating 330 by diffusing out from the coating, working their way through the entanglement of polymer chains 334 until the surface of the drug coating is reached, then furthering their discourse into the blood stream or local tissue bed where they are metabolized or otherwise absorbed into the body. Alternatively, dissolution of the polymer chains can result in the release of drug molecules 336.

By tailoring the interdispersed plasticizers and drugs, the concentration, distribution profile, and elution rates of bioactive agents or drugs can be controlled. In one embodiment, a higher concentration of plasticizers 338 are located closer to the stent framework and away from the outer surface of the stent coating. In this case, the release or elution of drug molecules 336 will tend to be constant over a longer period of time. Alternatively, a higher concentration of plasticizers 338 near the outer surface of the stent coating will tend to result in a large initial burst of drug. The distribution of the plasticizers and drugs can be tailored to fit the desired elution rate by controlling the concentration profile of the interdispersed plasticizers and drugs.

Figure 4:
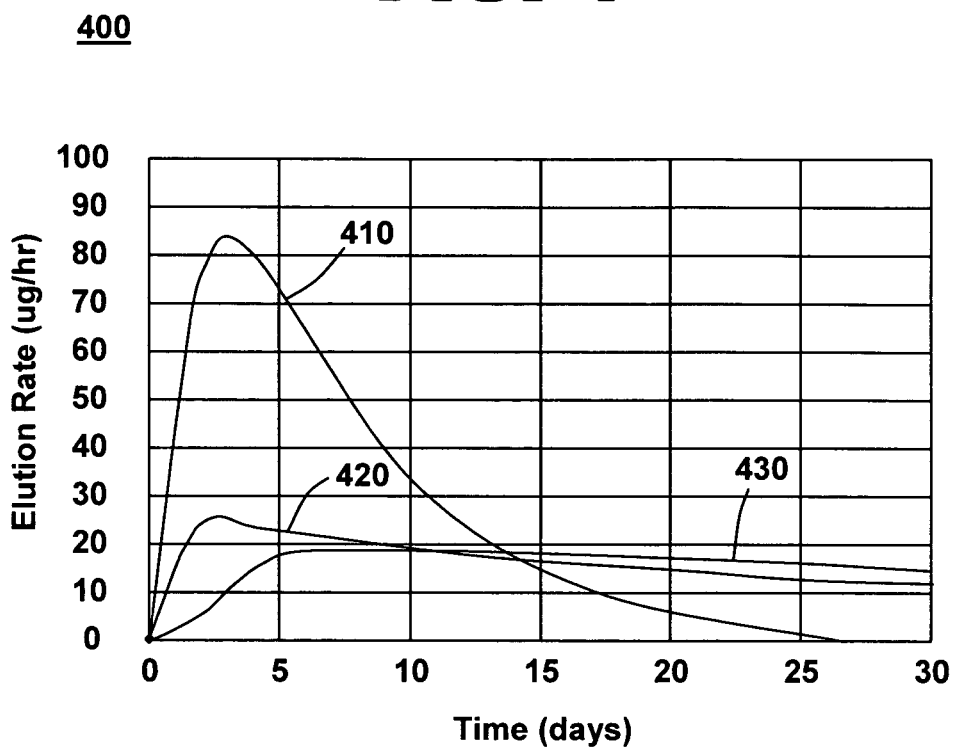
FIG. 4 is a graphical illustration of drug elution from a drug-polymer coated stent including at least one plasticizer, in accordance with one embodiment of the current invention.

FIG. 4 shows a graphical illustration of drug elution from a drug-polymer coated stent including at least one plasticizer, in accordance with one embodiment of the present invention at 400. Elution graph 400 shows characteristic elution rate curves 410 and 420 for a drug being released from a stent coating. Drug elution refers to the transfer of the bioactive agent out from the drug-polymer coated stent. The elution rate is determined as the amount of bioactive agent excreted out of the drug-polymer coating per unit time, typically measured in units of weight such as micrograms and units of time such as hours. In some cases, the bioactive agent diffuses out of the drug-polymer coating. In other cases, a portion of the polymeric coating is absorbed into the body and bioactive agents are released. One of the ways of speeding the transport of drug from the inner layers next to the stent framework is through the addition of a suitable plasiticizer in the inner layers of the stent coating. The release profile can be modulated by tailoring the distribution of plasticizers and drugs within the drug-polymer coating.

Elution rate curve 410 depicts an initially high elution rate for the first couple of days and a rapidly decaying elution rate over the next several weeks, for the case of a high concentration of plasticizers near the outer surface of the drug polymer.

Elution rate curve 420 depicts a flatter drug delivery rate, for the case of a higher concentration of plasticizers near the inner surface of the drug-polymer coating close to the stent framework. Other profiles can be achieved by controlling the distribution and concentration of the interdispersed drugs and plasticizers in the stent coating.

Elution rate curve 430 avoids the burst effect altogether, and has a more level elution rate over the first month. This elution rate profile can be achieved, for example, with a low or negligible concentration of drugs and plasticizers in a layer near the outside of the stent coating, with a higher concentration of drugs and plasticizers near the middle of the drug-polymer coating, and a higher concentration yet in layers closest to the stent framework.

FIG. 5 shows a flow diagram of a method of manufacturing a drug-polymer coated stent, in accordance with one embodiment of the present invention at 500. Manufacturing method 500 comprises various steps to manufacture drug-polymer coated stents.

A polymeric material is mixed with a suitable solvent to form a polymeric solution, as seen at block 510. The polymeric material comprises, for example, a biostable polymer, biodegradable polymer, or a biocompatible polymer for use on drug-polymer stents. The polymeric material may include, for example, a linear polymer such as polyethylene; a blocked copolymer such as a styrenic block copolymer; a terpolymer such as poly(hexyl methacrylate), vinyl acetate and vinyl pyrrolidinone; or a polymer blend such as polycarbonate-polycaprolactone. The solvent may be any suitable organic solvent capable of dissolving the polymeric material such as chloroform, tetrahydrofuran, methyl chloride, toluene, ethyl acetate, or dioxane.

One or more bioactive agents are mixed with the polymeric solution to form a drug-polymer solution. The bioactive agents may be added directly into the polymeric solution and mixed to form the drug-polymer solution. Alternatively, the bioactive agents may be dissolved in a bioactive agent solution comprising a suitable solvent, then mixed with the polymeric solution to form the drug-polymer solution. In either case, a suitable amount of bioactive agent or drug is added to the drug-polymer solution. Sufficient bioactive agents are added to achieve the desired pharmaceutical intent when deployed. The drug constituency within the drug-polymer coating is usually between 0.5 percent and 50 percent of the bioactive drug by weight.

A plasticizer is mixed and interdispersed within the polymeric solution to form a plasticized drug-polymer coating, as seen at block 520. The plasticizers may initially be in liquid or solid form, and then mixed or dissolved in the polymeric solution. The plasticizers may include, for example, lecithin, dibutyl sebacate, citric acid, an alcohol ester, polyethylene glycol, polypropylene glycol, a biostable plasticizer, a biocompatible plasticizer, a biodegradable plasticizer, or a combination thereof. The plasticizers may be added to the polymeric solution prior to or after the addition of the bioactive agents.

An adhesion layer may be applied onto the stent framework, as seen at block 530. The adhesion layer is applied prior to applying the plasticized drug-polymer coating. The adhesion layer includes a material such as, for example, parylene, polyurethane, phenoxy, epoxy, polyimide, polysulfone, pellathane, a suitable polymeric adhesion material, or a combination thereof. The stent framework typically includes a metallic or a polymeric base. The metallic base comprises a metal such as stainless steel, nitinol, tantalum, MP35N alloy, platinum, titanium, a suitable biocompatible alloy, a suitable biocompatible material, or any combination thereof. The polymeric base is any suitable polymer for biomedical stent applications, as is known in the art.

The plasticized drug-polymer coating is applied onto the stent framework, as seen at block 540. The plasticized drug-polymer coating may be applied using any suitable application technique such as dipping, spraying, brushing, painting or dispensing.

The thickness of the plasticized drug-polymer coating can vary, though is typically between 0.5 microns and 20 microns. Depending on the diameter and length of the stent, the weight of the plasticized drug-polymer coating is usually between 50 micrograms and 1500 micrograms for a range of stent sizes. Additional coats may be added to thicken the plasticized drug coating or to increase the drug dosage, if needed. Multiple coats of the plasticized drug-polymer coating may be applied with varying concentrations of plasticizers and various drugs, such that a tailored plasticizer and drug profile can be attained to aid in the control of the elution profile.

The plasticized drug-polymer coating is dried, as seen at block 550. The plasticized drug-polymer coating may be dried for example, by evaporating the solvent after application. The drying may be performed at room temperature and under ambient conditions. A nitrogen environment or other controlled environment may also be used. Alternatively, the drug-polymer solution can be dried by evaporating the majority of the solvent at room temperature, and further dried in a vacuum environment between room temperature of about 25 degrees centigrade and 45 degrees centigrade or higher to extract any pockets of solvent buried within the drug-polymer coating.

A barrier coating may be applied onto the plasticized drug-polymer coating, as seen at block 560. The barrier coating includes a material such as, for example, a polyurethane, a phenoxy, ethylene vinyl acetate, polycaprolactone, polylactide, fibrin, collagen, a biocompatible polymer, a biostable polymer, a biodegradable polymer, or a combination thereof. The barrier coating may be applied using any suitable application technique such as dipping, spraying, brushing, painting or dispensing. The barrier coating may be dried by heating the coated stent in a vacuum or inert environment at an elevated temperature.

Additional drug-polymer coatings may be applied to the plasticized drug-polymer coated stent. Additional barrier layers may be positioned between the drug-polymer layers to aid in the control of the elution rates of the incorporated drugs and bioactive agents.

Variants of the method for manufacturing a drug-polymer coated stent can be used, such as mixing the constituents into the same solution, using different solvents for each component, or altering the order of mixing stock solutions of each of the constituents.

In one exemplary method, the coated stents are reduced in diameter and placed into the distal end of the catheter. The process forms an interference fit, which secures the stent onto the catheter. The catheter with the stent may be placed in a catheter package and sterilized prior to shipping and storing. Sterilization of the stent using conventional procedures is completed typically before clinical use.

When ready for deployment, the drug-polymer coated stent including the bioactive agents and the grafted styrenic block copolymer is inserted into a vessel of the body. The drug-polymer coated stent is inserted typically in a controlled environment such as a catheter lab or hospital. The stent is deployed, for example, by expanding the stent with a balloon or by extracting a sheath to allow a self-expandable stent to enlarge after positioning the stent at the desired location within the body.

Once deployed, the drug-polymer coating elutes the bioactive agents into the body and particularly into the tissue bed surrounding the stent framework. The elution rates of the bioactive agents into the body are based on the type of plasticizer and drugs included in the plasticized drug-polymer coating, their distribution profile, and other factors.

EXAMPLE 1

Formulation

In this example, details of one formulation for coating a stent with a plasticized drug-polymer coating are described. Initially, 0.0373 grams of an antirestonotic agent is weighed and transferred into a small glass vial. An amount of polymeric material comprising poly(butyl methacrylate-co-methyl methacrylate), weighing 0.0448 grams, is transferred into the same glass vial with the antirestonotic agent. One source of poly(butyl methacrylate-co-methyl methacrylate) is provided by Sigma-Aldrich Corporation, of St. Louis, Mo., catalog number 47403-7. An amount of polybutylmethacrylate, weighing 0.0671 grams, is transferred into the same glass vial with antirestonotic agent. Ten milliliters of chloroform is added to the glass vial and the polymeric mixture in the vial is shaken until all materials are dissolved. An amount of dibutyl sebacate equal to 0.0134 grams is added to the vial and shaken to get a uniform solution. The polymer solution is applied onto a metallic stent, using a technique such as spraying. The stent used in this example is an eighteen-millimeter long S670 stent made by Medtronic Ave, Santa Rosa, Calif. The plasticized drug-polymer coating is then dried. The target weight of the applied drug polymer, in this example, is 800 micrograms.

Although the present invention applies to cardiovascular and endovascular stents with timed-release pharmaceutical drugs, the use of plasticizers in polymer-drug coatings and other polymer coatings may be applied to other implantable and blood-contacting biomedical devices such as coated pacemaker leads, microdelivery pumps, feeding and delivery catheters, heart valves, artificial livers and other artificial organs.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vascular condition, comprising:
a catheter;
a stent operably coupled to the catheter, the stent including a stent framework; and
a drug-polymer coating operably disposed on the stent framework, the drug-polymer coating having an inner coating surface and an outer coating surface, the drug-polymer coating including polymer chains and at least one plasticizer dispersed within the drug-polymer coating, wherein a concentration of the at least one plasticizer varies between the inner coating surface and the outer coating surface.

2. The system of claim 1 wherein the drug-polymer coating comprises a bioactive agent to provide a therapeutic characteristic.

3. The system of claim 2 wherein the bioactive agent is selected from the group consisting of antirestonotic agent, an antineoplastic agent, an antiproliferative agent, an antisense agent, an antiplatelet agent, an antithrombogenic agent, an anticoagulant, an antibiotic, an anti-inflammatory agent, a gene therapy agent, an organic drug, a pharmaceutical compound, a recombinant DNA product, a recombinant RNA product, a collagen, a collagenic derivative, a protein, a protein analog, a saccharide, a saccharide derivative, and a combination thereof.

4. The system of claim 1 wherein the plasticizer comprises lecithin.

5. The system of claim 1 wherein the plasticizer is selected from the group consisting of dibutyl sebacate, citric acid, an alcohol ester, polyethylene glycol, polypropylene glycol, a biostable plasticizer, a biocompatible plasticizer, a biodegradable plasticizer, and a combination thereof.

6. The system of claim 1 wherein the plasticized drug-polymer coating has a thickness between 0.1 microns and 50 microns.

7. The system of claim 1 wherein the catheter includes a balloon used to expand the stent.

8. The system of claim 1 wherein the catheter includes a sheath that retracts to allow expansion of the stent.

9. The system of claim 1 wherein the stent framework comprises a metallic base.

10. The system of claim 9 wherein the metallic base is selected from the group consisting of stainless steel, nitinol, tantalum, MP35N alloy, platinum, titanium, a suitable biocompatible alloy, a suitable biocompatible material, and a combination thereof.

11. The system of claim 1 wherein the stent framework comprises a polymeric base.

12. The system of claim 1 further comprising:
an adhesion layer positioned between the stent framework and the drug-polymer coating.

13. The system of claim 12 wherein the adhesion layer comprises a material selected from the group consisting of parylene, polyurethane, phenoxy, epoxy, polyimide, polysulfone, pellathane, a suitable polymeric adhesion material, and a combination thereof.

14. The system of claim 12 wherein the adhesion layer has a thickness between 0.1 microns and 2.0 microns.

15. The system of claim 1 further comprising:
a barrier coating covering the plasticized drug-polymer coating.

16. The system of claim 15 wherein the barrier coating is selected from the group consisting of a polyurethane, a phenoxy, ethylene vinyl acetate, polycaprolactone, polylactide, fibrin, collagen, a biocompatible polymer, a biostable polymer, a biodegradable polymer, and a combination thereof.

17. The system of claim 15 wherein the barrier coating has a thickness between 0.1 microns and 10 microns.

18. The system of claim 1 wherein the concentration of the at least one plasticizer is a higher concentration located closer to the inner coating surface and away from the outer coating surface of the stent coating.

19. The system of claim 1 wherein the concentration of the at least one plasticizer is a higher concentration located closer to the outer coating surface and away from the inner coating surface of the stent coating.

20. The system of claim 1 wherein the drug-polymer coating includes a first concentration of plasticizer in an outer layer near the outside of the stent coating, a second concentration of plasticizer in an inner layer closest to the stent framework and a third concentration in an intermediate layer disposed between the outer layer and the inner layer, wherein the first concentration is lower than the second concentration and the third concentration is an intermediate concentration between the first concentration and the second concentration.

21. The system of claim 1 wherein the drug-polymer coating includes a first concentration of plasticizer in an outer layer near the outside of the stent coating, a second concentration of plasticizer in an inner layer closest to the stent framework and a third concentration in an intermediate layer disposed between the outer layer and the inner layer, wherein the first concentration is higher than the second concentration and the third concentration is an intermediate concentration between the first concentration and the second concentration.

22. A drug-polymer coated stent, comprising:
a stent framework; and
a plasticized drug-polymer coating on the stent framework, the plasticized drug-polymer coating having an inner coating surface and an outer coating surface, the plasticized drug-polymer coating including polymer chains and at least one plasticizer dispersed within the plasticized drug-polymer coating, wherein a concentration of the at least one plasticizer varies between the inner coating surface and the outer coating surface.

23. The drug-polymer coated stent of claim 22 wherein the plasticized drug-polymer coating comprises a plasticizer selected from the group consisting of lecithin, dibutyl sebacate, citric acid, an alcohol ester, polyethylene glycol, polypropylene glycol, a biostable plasticizer, a biocompatible plasticizer, a biodegradable plasticizer, and a combination thereof.

24. The drug-polymer coated stent of claim 22 further comprising:
an adhesion layer positioned between the stent framework and the drug-polymer coating.

25. The drug-polymer coated stent of claim 22 further comprising:
a barrier coating covering the plasticized drug-polymer coating.

26. A method of manufacturing a drug-polymer coated stent, comprising:
mixing a polymeric material with a solvent to form a polymeric solution;
interdispersing a plasticizer in the polymeric solution to form a plasticized drug-polymer coating;
applying the plasticized drug-polymer coating onto a stent framework; and
drying the plasticized drug-polymer coating,
wherein the applied plasticized drug-polymer coating has an inner coating surface and an outer coating surface and wherein a concentration of the plasticizer varies between the inner coating surface and the outer coating surface.

27. The method of claim 26 wherein the plasticizer is selected from the group consisting of lecithin, dibutyl sebacate, citric acid, an alcohol ester, polyethylene glycol, polypropylene glycol, a biostable plasticizer, a biocompatible plasticizer, a biodegradable plasticizer, and a combination thereof.

28. The method of claim 26 further comprising:
applying an adhesion layer onto the stent framework, wherein the adhesion layer is applied prior to applying the plasticized drug-polymer coating.

29. The method of claim 28 wherein the adhesion layer comprises a material selected from the group consisting of parylene, polyurethane, phenoxy, epoxy, polyimide, polysulfone, pellathane, a suitable polymeric adhesion material, and a combination thereof.

30. The method of claim 26 further comprising:
applying a barrier coating onto the plasticized drug-polymer coating.

31. The method of claim 30 wherein the barrier coating is selected from the group consisting of a polyurethane, a phenoxy, ethylene vinyl acetate, polycaprolactone, polylactide, fibrin, collagen, a biocompatible polymer, a biostable polymer, a biodegradable polymer, and a combination thereof.

* * * * *